US008846069B2

(12) United States Patent
Hossainy et al.

(10) Patent No.: US 8,846,069 B2
(45) Date of Patent: Sep. 30, 2014

(54) COATINGS FOR IMPLANTABLE DEVICES COMPRISING POLYMERS OF LACTIC ACID AND METHODS FOR FABRICATING THE SAME

(75) Inventors: Syed F.A. Hossainy, Hayward, CA (US); Yiwen Tang, San Jose, CA (US); Eugene T. Michal, San Francisco, CA (US); Thierry Glauser, Redwood City, CA (US); Stephen D. Pacetti, San Jose, CA (US); Jessica DesNoyer, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 399 days.

(21) Appl. No.: 12/762,718

(22) Filed: Apr. 19, 2010

(65) Prior Publication Data

US 2011/0027336 A1 Feb. 3, 2011

Related U.S. Application Data

(63) Continuation-in-part of application No. 10/718,976, filed on Nov. 20, 2003, now abandoned.

(51) Int. Cl.
*A61F 13/00* (2006.01)
*A61L 31/10* (2006.01)
*A61L 31/14* (2006.01)
*A61L 31/16* (2006.01)

(52) U.S. Cl.
CPC ............. *A61L 31/16* (2013.01); *A61L 31/10* (2013.01); *A61L 31/148* (2013.01); *A61F 2250/0067* (2013.01)
USPC ............ 424/422; 424/423; 424/424; 424/425

(58) Field of Classification Search
None
See application file for complete search history.

(56) References Cited

U.S. PATENT DOCUMENTS

| 4,733,665 | A | | 3/1988 | Palmaz |
| 4,800,882 | A | | 1/1989 | Gianturco |
| 4,886,062 | A | | 12/1989 | Wiktor |
| 5,548,035 | A | * | 8/1996 | Kim et al. ...................... 525/408 |
| 5,824,048 | A | | 10/1998 | Tuch et al. |
| 6,113,943 | A | | 9/2000 | Okada et al. |
| 6,258,121 | B1 | * | 7/2001 | Yang et al. ................... 623/1.46 |
| 6,555,157 | B1 | | 4/2003 | Hossainy |
| 6,753,071 | B1 | | 6/2004 | Pacetti |
| 6,783,793 | B1 | | 8/2004 | Hossainy et al. |
| 2003/0203000 | A1 | | 10/2003 | Schwarz et al. |
| 2007/0212393 | A1 | * | 9/2007 | Patravale et al. .............. 424/423 |
| 2008/0015686 | A1 | * | 1/2008 | Gale et al. .................... 623/1.38 |

FOREIGN PATENT DOCUMENTS

| EP | 1 362 603 | 11/2003 |
| EP | 1 932 551 | 5/2008 |
| WO | WO 02/34311 | 5/2002 |
| WO | WO 03/035131 | 5/2003 |
| WO | WO 2005/051449 | 6/2005 |

OTHER PUBLICATIONS

Sobczak et al. "Polymerization of cyclic esters using amino acid initiators" 2008, Journal of Macromolecular Science Part A: Pure and Applied Chemistry, 45, pp. 872-877.*
International Search Report and Written Opinion for PCT/US2011/032790, mailed Oct. 5, 2011, 4 pgs.
International Search Report and Written Opinion for PCT/US2004/038843 filed Nov. 17, 2004, mailed Apr. 21, 2005, 11 pgs.
European Search Report for 08001182.8-2123, mailed Apr. 2, 2008, 7 pgs.
Schmidmaier et al., *A New Biodegradable Polylactic Acid Coronary Stent-Coating, Releasing PEG-Hirudin and a Prostacycline Analog, Reduces Both Platelet Activation and Plasmatic Coagulation*, J. of Am. College of Cardiology, vol. 29, No. 2 Suppl., Mar. 16, 1997, p. 354A.
Schmidmaier et al., *Time Release Characteristics of a Biodegradable Stent Coating with Polylactic Acid Releasing PEG-Hirudin and PG12-Analog*, J. of Am. College of Cardiology, vol. 29, No. 1 Suppl., Feb. 1997, p. 94A.

* cited by examiner

*Primary Examiner* — James Rogers
(74) *Attorney, Agent, or Firm* — Squire Patton Boggs (US) LLP

(57) ABSTRACT

Coatings for an implantable medical device and a method of fabricating thereof are disclosed, the coatings comprising polymers of lactic acid.

18 Claims, No Drawings

COATINGS FOR IMPLANTABLE DEVICES COMPRISING POLYMERS OF LACTIC ACID AND METHODS FOR FABRICATING THE SAME

CROSS-REFERENCE

This application is a continuation-in-part of U.S. application Ser. No. 10/718,976 filed on Nov. 20, 2003, the teaching of which is incorporated by reference in its entirety.

BACKGROUND

1. Field of the Invention

This invention is directed to coatings for drug delivery devices, such as drug eluting vascular stents, and methods for producing the same.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Vasospasm can occur, which although temporary, can lead to the patient experiencing chest pains and other symptoms. Moreover, thrombosis and restenosis of the artery may develop over several months after the procedure, which may require another angioplasty procedure or a surgical by-pass operation. To reduce the partial or total occlusion of the artery by the collapse of arterial lining or vasospasm, and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Local administration of therapeutic agents via stents has shown some favorable results in reducing restenosis. However, there is a great need for better and more effective coatings for the local drug delivery. For example, it is desirable to have biologically absorbable stent coatings possessing biologically beneficial properties, enhanced absorption rate, a drug release rate that can be modulated, and good mechanical properties. Embodiments of the present invention disclose such coatings.

SUMMARY

A medical article comprising an implantable substrate having a coating is provided, the coating includes a first biologically absorbable polymer comprising poly(lactic acid), derivatives thereof, or block-copolymers having at least one moiety derived from poly(lactic acid). The block-copolymers include diblock-copolymers, triblock-copolymers, or mixtures thereof, such as the diblock-copolymers and triblock-copolymers having at least one biocompatible moiety. Examples of biocompatible moieties include poly(ethylene glycol), poly(ethylene oxide), polypropylene glycol), poly (tetramethylene glycol), poly(ethylene oxide-co-propylene oxide, $\epsilon$-caprolactone, $\beta$-butyrolactone, $\delta$-valerolactone, glycolide, poly(N-vinyl pyrrolidone), poly(acrylamide methyl propane sulfonic acid) and salts thereof, poly(styrene sulfonate), sulfonated dextran; polyphosphazenes, poly(orthoesters), poly(tyrosine carbonate), hyaluronic acid or derivatives thereof, copolymers of poly(ethylene glycol) with hyaluronic acid or derivatives thereof, heparin, copolymers of polyethylene glycol with heparin, a graft copolymer of poly (L-lysine) and poly(ethylene glycol).

A method for fabricating a medical article is provided, the method includes applying a coating on at least a portion of an implantable substrate, the coating including a first biologically absorbable polymer comprising poly(lactic acid), derivatives thereof, or block-copolymers having at least one moiety derived from poly(lactic acid).

DETAILED DESCRIPTION

1. Terms and Definitions

The following definitions apply:

The terms "biologically degradable," "biologically erodable," "biologically absorbable," and "biologically resorbable" coatings and/or polymers, which are used interchangeably, are defined as coatings and/or polymers that are capable of being completely degraded, dissolved, and/or eroded over time when exposed to bodily fluids such as blood and are gradually resorbed, absorbed and/or eliminated by the body. The processes of breaking down and eventual absorption and elimination of the coating and/or polymer can be caused, for example, by hydrolysis, metabolic processes, bulk or surface erosion, and the like.

Whenever the reference is made to "biologically degradable," "biologically erodable," "biologically absorbable," and "biologically resorbable" stent coatings and/or polymers forming such stent coatings, it is understood that after the process of degradation, erosion, absorption, and/or resorption has been completed, no coating will remain on the stent.

Whenever the terms "degradable," "biodegradable," or "biologically degradable" are used in this application, they are intended to broadly include biologically degradable, biologically erodable, biologically absorbable, and biologically resorbable coatings and/or polymers.

"Biodegradability," "bioerodability," "bioabsorbability," and "bioresorbability" are defined as inherent properties of the coating and/or polymer making the coating and/or polymer biologically degradable, biologically erodable, or biologically absorbable, and biologically resorbable.

"Fast release" is defined as in vivo release of substantially entire amount of the drug from the stent coating in less than 15 days, for example, within 7 to 14 days. "Slow release" is defined as in vivo release of substantially entire amount of the drug from the stent coating in 15 days or longer, for example, within 15 to 56 days.

The terms "block-copolymer" and "graft copolymer" are defined in accordance with the terminology used by the International Union of Pure and Applied Chemistry (IUPAC). "Block-copolymer" refers to a copolymer containing a linear arrangement of blocks. The block is defined as a portion of a polymer molecule in which the monomeric units have at least one constitutional or configurational feature absent from the adjacent portions. "Graft copolymer" refers to a polymer composed of macromolecules with one or more species of block connected to the main chain as side chains, these side chains having constitutional or configurational features that differ from those in the main chain.

The term "AB block-copolymer" is defined as a block-copolymer having moieties A and B arranged according to the general formula $-\{[A-]_m[B]_n\}-_x$, where each of "m," "n," and "x" is a positive integer, and m≥2, and n≥2.

The term "ABA block-copolymer" is defined as a block-copolymer having moieties A and B arranged according to the general formula $-\{[A-]_m[B]_n\}-[A]_p\}-_x$, where each of "m," "n," "p," and "x" is a positive integer, and m≥2, and n≥2, and p≥2.

The blocks of the ABA and AB block-copolymers need not be linked on the ends, since the values of the integers determining the number of A and B blocks are such as to ensure that the individual blocks are usually long enough to be considered polymers in their own right. Accordingly, the ABA block copolymer can be named poly A-block-co-poly B block-co-poly A block-copolymer, and the AB block copolymer can be named poly A-block-co-poly B block-copolymer. Blocks "A" and "B," typically, larger than three-block size, can be alternating or random.

2. Embodiments of the Invention

A coating for an implantable medical device, such as a stent, according to embodiments of the present invention, can be a multi-layer structure that can include any of the following four layers or combination thereof:
 (a) a primer layer;
 (b) a drug-polymer layer (also referred to as "reservoir" or "reservoir layer") or alternatively a polymer free drug layer;
 (c) a topcoat layer; and/or
 (d) a finishing coat layer.

Each layer of the stent coating can be formed on the stent by dissolving the polymer or a blend of polymers in a solvent, or a mixture of solvents, and applying the resulting polymer solution on the stent by spraying or immersing the stent in the solution. After the solution has been applied onto the stent, the coating is dried by allowing the solvent to evaporate. The process of drying can be accelerated if the drying is conducted at an elevated temperature. The complete stent coating can be optionally annealed at a temperature between about 40° C. and about 150° C. for a period of time about 5 minutes and about 60 minutes, if desired, to improve the thermodynamic stability of the coating.

To incorporate a drug into the reservoir layer, the drug can be combined with the polymer solution that is applied onto the stent as described above. Alternatively, if it is desirable to have the stent coating with the fast drug release rate, a polymer-free reservoir can be made. To fabricate a polymer free reservoir, the drug can be dissolved in a suitable solvent or mixture of solvents, and the resulting drug solution can be applied on the stent by spraying or immersing the stent in the drug solution.

Instead of introducing the drug as a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. The suspension can be mixed with a polymer solution and the mixture can be applied on the scent as described above. Alternatively, the drug suspension can be applied on the stent without being mixed with the polymer solution.

The drug-polymer layer can be applied directly onto at least a part of the stent surface to serve as a reservoir for at least one active agent or a drug which is incorporated into the reservoir layer. The optional primer layer can be applied between the stent and the reservoir to improve the adhesion of the drug-polymer layer to the stent. The optional topcoat layer can be applied over at least a portion of the reservoir layer and serves as a rate limiting membrane which helps to control the rate of release of the drug. In one embodiment, the topcoat layer can be essentially free from any active agents or drugs. If the topcoat layer is used, the optional finishing coat layer can be applied over at least a portion of the topcoat layer for further control of the drug release rate and for improving the biocompatibility of the coating. Without the topcoat layer, the finishing coat layer can be deposited directly on the reservoir layer.

The process of the release of the drug from a coating having both topcoat and finishing coat layers includes at least three steps. First, the drug is absorbed by the polymer of the topcoat layer on the drug-polymer layer/topcoat layer interface. Next, the drug diffuses through the topcoat layer using the void volume between the macromolecules of the topcoat layer polymer as pathways for diffusion. Next, the drug arrives to the topcoat layer/finishing layer interface. Finally, the drug diffuses through the finishing coat layer in a similar fashion, arrives to the outer surface of the finishing coat layer, and desorbs from the outer surface. At this point, the drug is released into the vessel wall or blood stream. Consequently, a combination of the topcoat and finishing coat layers, if used, can serve as a rate limiting barrier. The drug can be released through the degradation, dissolution, and/or erosion of the layer.

In one embodiment, any or all of the layers of the stent coating, can be made of a biologically degradable, erodable, absorbable, and/or resorbable polymer. In another embodiment, the outermost layer of the coating can be limited to such a polymer.

To illustrate in more detail, in the stent coating having all four layers described above (i.e., the primer, the reservoir layer, the topcoat layer and the finishing coat layer), the outermost layer is the finishing coat layer, which is made of a polymer that is biologically degradable, erodable, absorbable, and/or resorbable. In this case, optionally, the remaining layers (i.e., the primer, the reservoir layer, the topcoat layer) can be also fabricated of a biologically degradable polymer; and the polymer can be the same or different in each layer.

If the finishing coat layer is not used, the topcoat layer can be the outermost layer and is made of a biologically degradable polymer. In this case, optionally, the remaining layers (i.e., the primer and the reservoir layer) can be also fabricated of a biologically degradable polymer; and the polymer can be the same or different in each of the three layers.

If neither the finishing coat layer nor the topcoat layer is used, the stent coating can have only two layers, the primer and the reservoir. The reservoir in this case is the outermost layer of the stent coating and is made of a biologically degradable polymer. Optionally, the primer can be also fabricated of a biologically degradable polymer. The two layers can be made from the same or different polymers.

The biological degradation, erosion, absorption and/or resorption of a biologically degradable, erodable, absorbable and/or resorbable polymer are expected to cause the increase of the release rate of the drug due to the gradual disappearance of the polymer that forms the reservoir or the topcoat layer, or both. By choosing an appropriate degradable polymer, coating formulation and processing conditions, the stent coating can be engineered to provide either fast or slow release of the drug, as desired. Those having ordinary skill in the art can determine whether a stent coating having slow or fast release rate is advisable for a particular drug. For example, fast release may be recommended for stent coatings loaded with antimigratory drugs which often need to be released within 1 to 2 weeks. For antiproliferative drugs, slow release may be needed (up to 30 days release time).

Biologically degradable, erodable, absorbable and/or resorbable polymers that can be used for making any of the stent coating layers include at least one of poly(lactic acids), i.e., poly(D,L-lactic acid) (DLPLA), poly(D-lactic acid) or poly(L-lactic acid), or any combination thereof. Poly(lactic acid) has the formula H—[O—CH(CH$_3$)—C(O)]$_n$—OH and can be obtained by acid based condensation of lactic acid. Poly(lactide), which has the same polymer backbone structure as poly(lactic acid) can be obtained by ring-opening polymerization of lactide (a cyclic dimer of lactic acid), as demonstrated schematically by reaction (I), where lactide is compound (A) and poly(lactic acid) is compound (B):

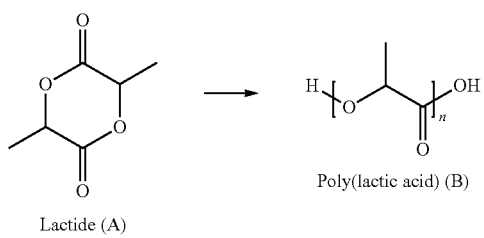

Lactide (A)   Poly(lactic acid) (B)

(I)

In this description, the terms poly(lactide) and poly(lactic acid) may be used interchangeably. The backbone structures are identical, the difference being the starting material used to make the polymer, lactide versus lactic acid. The molecular weight of poly(lactic acid) can be between about 30,000 and about 300,000 Daltons, corresponding to the value of the integer n in the compound (B) between about 416 and about 4,166. Typically, a Lewis acid catalyst, such as stannous octoate, is used to catalyze the reaction and facilitates the formation of higher molecular weight polymer. Those having ordinary skill in the art can determine the conditions under which the transformation of lactide to poly(lactic acid) illustrated by reaction (I) can be carried out.

Alternatively, polymers containing moieties derived from poly(lactic acid) can be also used in addition to or instead of poly(lactic acid) for making any of the stent coating layers. One type of alternative polymers based on poly(lactic acid) includes derivatives of poly(lactic acid), for example, hydrolyzed or carboxylated poly(lactic acid), or a blend thereof. Using the hydrolyzed or carboxylated poly(lactic acid) is expected to result in the increased rate of degradation of the coating, consequently leading to the increased rate of release of the drug.

The hydrolyzed poly(lactic acid) is a polymeric product comprising a mixture of the original (unhydrolyzed) poly(lactic acid) (B) and oligomeric and/or polymeric products of the hydrolysis thereof. The products of hydrolysis can include a complex mixture of oligomers of lactic acid, some monomeric lactic acid and other products that can include hydroxylated species. The mixture can contain between about 1 mass % and about 20 mass % original poly(lactic acid) (B) having the molecular weight as indicated above, and the balance, the products of hydrolysis thereof. The oligomeric and/or polymeric products of hydrolysis of poly(lactic acid) can have an average molecular weight between about 1,000 and about 20,000 Daltons.

To obtain the hydrolyzed poly(lactic acid), poly(lactic acid) can be hydrolyzed under the conditions that can be selected by those having ordinary skill in the art. The process of hydrolysis is a polymer-analogous transformation and can be carried out until the mixture of poly(lactic acid) and the products of hydrolysis thereof are obtained, the mixture having a desired ratio between poly(lactic acid) and the products of hydrolysis thereof. The desired ratio can be also determined by those having ordinary skill in the art.

The carboxylated poly(lactic acid) comprises poly(lactic acid) terminated with a carboxyl group and can be obtained by ring-opening polymerization of lactide (A), in the presence of a hydroxy acid HO—R—COOH serving as a ring opening agent as demonstrated schematically by reaction (II), where the carboxylated poly(lactic acid) is compound (C):

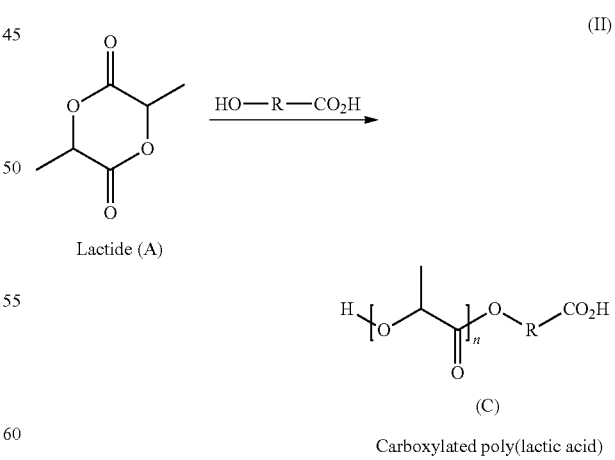

Lactide (A)

(C)

Carboxylated poly(lactic acid)

(II)

Hydroxy acid HO—R—COOH, the ring-opening agent, in reaction (II) can be any suitable hydroxy acid that can be selected by those having ordinary skill in the art. One example of hydroxy acid that can be used is hydroacetic (glycolic) acid.

In some embodiments, the ring opening agent is of formula HX—R—COOH, wherein X can be O, NH, or S; R can be a straight chain or branched alkyl group of 2 to 20 carbons, wherein the alkyl group is unsubstituted or substituted. The substituents include but are not limited to hydroxyl, amino, sulfhydryl, oxo, carboxyl, and phenyl group. R can comprise an aromatic group such as a phenyl group or a substituted phenyl group. The ring-opening reaction is demonstrated in the following scheme:

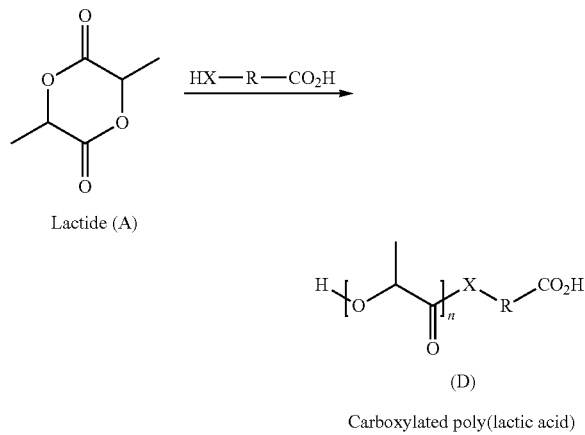

Lactide (A)

(D)

Carboxylated poly(lactic acid)

In some embodiments, the ring-opening agent is a hydroxy acid of formula HO—R—COOH, R can be straight chain or branched, unsubstituted or substituted alkyl group. The hydroxyl acids include, but are not limited to, alpha-hydroxy acid, beta-hydroxy acid, and gamma-hydroxy acid. Exemplary hydroxyl acids include, but are not limited to, glycolic acid, 2-hydroxypropionic acid, 3-hydroxypriopionic acid, 2,3-dihydroxypropanoic acid (glyceric acid), 2-hydroxybutyric acid, 3-hydroxybutyric acid, 4-hydroxybutyric acid, hydroxybutanedioic acid (malic acid), 2,3-dihyroxybutanedioic acid (tartaric acid), 3-hydroxy-2-oxopropanoic acid (hydroxypyruvate), 3-hydroxy-2-methylpropanoic acid, 3-hydroxypentanoic acid (3-hydroxyvaleric acid), 4-hydroxypentanoic acid, 5-hydroxypentanoic acid, dihyroxypentanoic acid, 2-hydroxypentanedioic acid (alpha-hydroxylglutaric acid), 2,3,4,5, and 6-hydroxyhexanic acid, and tartaric acid.

In some embodiments, in the hydroxy acid HO—R—COOH, R can comprise an aromatic group such as phenyl group. Such hydroxyl acids include, but not limited to, hydroxyalkyl substituted benzoic acid such as 2,3, or 4-hydroxymethyl benzoic acid, and 2-phenyl-2-hydroxy acetic acid (mandelic acid).

In some embodiments, the ring-opening agent can be an amino acid of formula $H_2N$—R—COOH. The amino acid can be a natural occurring amino acid or an artificial amino acid. The ring-opening polymerization using this ring-opening agent produces a carboxylated poly(lactic acid) of formula (E):

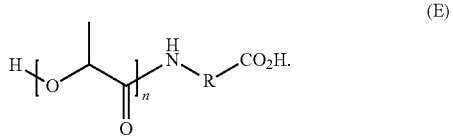

(E)

In some embodiments, the ring-opening agent can be a sulfhydryl acid of formula HS—R—COOH. The ring-opening polymerization using this ring-opening agent produces a carboxylated poly(lactic acid) of formula (F):

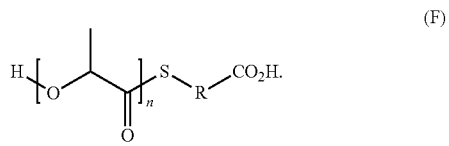

(F)

The carboxylated poly(lactic acid) can be a fully carboxylated poly(lactic acid), i.e., can be a 100% product (C). The molecular weight of the fully carboxylated poly(lactic acid) can be between about 1,000 and about 20,000 Daltons. The fully carboxylated poly(lactic acid) can be obtained from Birmingham Polymers, Inc. of Birmingham, Ala.

The carboxylated poly(lactic acid) can be also in a mixture with original poly(lactic acid) (B). The mixture can contain between about 1 mass % and about 20 mass % original poly(lactic acid) (B) having the molecular weight as indicated above, and the balance, the carboxylated poly(lactic acid) (C).

Another type of alternative polymers based on poly(lactic acid) that can be used includes block-copolymers, such as AB block-copolymers ("diblock-copolymers") or ABA block-copolymers ("triblock-copolymers"), or mixtures thereof. The molecular weight of block A can be between about 300 and about 40,000 Daltons, more narrowly, between about 8,000 and about 30,000 Daltons, for example, about 15,000 Daltons. The molecular weight of block B can be between about 50,000 and about 250,000 Daltons, more narrowly, between about 80,000 and about 200,000 Daltons, for example, about 100,000 Daltons.

Both ABA and AB block-copolymers that can be used contain the block(s) of poly(lactic acid), and the block(s) of a biologically compatible moiety, providing the AB or ABA block-copolymer with blood compatibility ("a biocompatible moiety"). To illustrate, in one embodiment, moiety A is poly(lactic acid) and moiety B is the biocompatible moiety. In another embodiment, moiety B is poly(lactic acid), and moiety A is the biocompatible moiety. In one embodiment, the biocompatible moieties are selected in such a way so that to make the entire ABA and AB block-copolymers biologically degradable.

Examples of suitable biocompatible moieties include poly(alkylene glycols), for example, poly(ethylene glycol) (PEG), poly(ethylene oxide), polypropylene glycol) (PPG), poly(tetramethylene glycol), or poly(ethylene oxide-co-propylene oxide); lactones and lactides, for example, ε-caprolactone, β-butyrolactone, δ-valerolactone, or glycolide; poly(N-vinyl pyrrolidone); poly(acrylamide methyl propane sulfonic acid) and salts thereof (AMPS and salts thereof); poly(styrene sulfonate); sulfonated dextran; polyphosphazenes; poly(orthoesters); poly(tyrosine carbonate); hyaluronic acid; hyaluronic acid having a stearoyl or palmitoyl substitutent group; copolymers of PEG with hyaluronic acid or with hyaluronic acid-stearoyl, or with hyaluronic acid-palmitoyl; heparin; copolymers of PEG with heparin; a graft copolymer of poly(L-lysine) and PEG; or copolymers thereof. A molecular weight of a suitable biocompatible polymeric moiety can be below 40,000 Daltons to ensure the renal clearance of the compound, for example, between about 300 and about 40,000 Daltons, more narrowly, between about 8,000 and about 30,000 Daltons, for example, about 15,000 Daltons. Lactones and lactides mentioned above can also replace a part or all of DLPLA in the block-copolymer, if desired.

Accordingly, one example of the AB block copolymer that can be used is poly(D,L-lactic acid)-block-poly(ethylene-glycol) (DLPLA-PEG). One possible structure of the DLPLA-PEG block-copolymer is shown by formula (III):

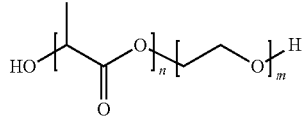
(III)

The DLPLA-PEG block-copolymer shown by formula (III) can have a total molecular weight between about 30,000 and about 300,000 Daltons, for example, about 60,000 Daltons as measured by the gel-permeation chromatography (GPC) method in tetrahydrofuran. The molecular weight of the PEG blocks can be between about 500 and about 30,000 Daltons, for example, about 550 Daltons, and the molecular weight of the DLPLA blocks can be between about 1,500 and about 20,000 Daltons, for example, about 1,900 Daltons. Accordingly, in formula (III), "n" is an integer that can have a value between about 21 and about 278, and "m" is an integer that can have a value between about 11 and about 682.

One example of the ABA block copolymer that can be used is poly(D,L-lactic acid) block-poly(ethylene-glycol)-block-poly(D,L-lactic acid) (DLPLA-PEG-DLPLA). One possible structure of the DLPLA-PEG-DLPLA block-copolymer is shown by formula (IV):

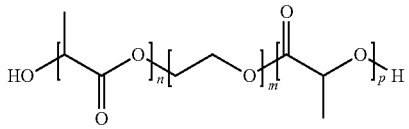
(IV)

The DLPLA-PEG-DLPLA block-copolymer shown by formula (IV) can have a total molecular weight between about 30,000 and about 300,000 Daltons, for example, about 60,000 Daltons as measured by the GPC method in tetrahydrofuran. The molecular weight of the PEG blocks can be between about 500 and about 30,000 Daltons, for example, about 7,500 Daltons, and the molecular weight of the DLPLA blocks can be between about 1,500 and about 20,000 Daltons, for example, one terminal DLPLA block can have the molecular weight of about 3,400 Daltons, and the other terminal DLPLA block can have the molecular weight of about 10,000 Daltons. Accordingly, in formula (IV), "n" is an integer that can have a value between about 21 and about 278, "m" is an integer that can have a value between about 11 and about 682, and "p" is an integer that can have a value between about 21 and about 278.

If desired, the positions of the moieties can be switched to obtain a BAB block-copolymer, poly(ethylene-glycol)-block-poly(D,L-lactic acid)-block-poly(ethylene-glycol) (PEG-DLPLA-PEG). One possible structure of the PEG-DLPLA-PEG block-copolymer is shown by formula (V) or (VI):

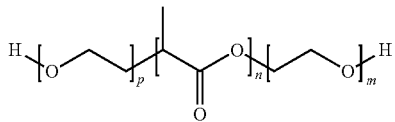
(V)

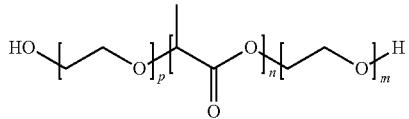
(VI)

The PEG-DLPLA-PEG block-copolymer shown by formula (V) or (VI) can have a total molecular weight between about 30,000 and about 300,000 Daltons, for example, about 60,000 Daltons as measured by the GPC method in tetrahydrofuran. The molecular weight of the PEG blocks can be between about 500 and about 30,000 Daltons, for example, about 7,500 Daltons, and the molecular weight of the DLPLA blocks can be between about 1,500 and about 20,000 Daltons. Accordingly, in formula (V), "n" is an integer that can have a value between about 21 and about 278, "m" is an integer that can have a value between about 11 and about 682, and "p" is an integer that can have a value between about 11 and about 682.

Block-copolymers shown by formulae (III-V) can be synthesized by standard methods known to those having ordinary skill in the art, for example, copolycondensation of PEG with DLPLA. The process of copolycondensation can be catalyzed by an acid or a base, if necessary.

According to one embodiment, hydrolyzed block copolymers of PEG and DPLA can be used for making the stent coatings. Both AB and ABA and BAB block-copolymers discussed above can be used to obtain the hydrolyzed block copolymers of PEG and DPLA. The hydrolyzed block copolymers of PEG and DPLA are polymeric products comprising a mixture of block copolymers of PEG and DPLA and products of partial hydrolysis thereof. The mixture can contain between about 1 mass % and about 20 mass % unhydrolyzed block copolymers of PEG and DPLA and the balance, the products of hydrolysis thereof.

To obtain the hydrolyzed block copolymers of PEG and DPLA, the block-copolymers can be hydrolyzed under the conditions that can be selected by those having ordinary skill in the art. The process of hydrolysis can be carried out until the mixture of the block-copolymer and the products of partial hydrolysis thereof is obtained, the mixture having a desired ratio between the block-copolymer and the products of partial hydrolysis thereof. The desired ratio can be also determined by those having ordinary skill in the art.

In accordance with other embodiments of the present invention, in addition to, or instead of, the polymers based on poly(lactic) acid, other biologically absorbable polymers can be used for making stent coatings. Some examples of such polymers include:
(a) poly(hydroxybutyrate) (PHB);
(b) poly(hydroxyvalerate) (PHV);
(c) poly(hydroxybutyrate-co-valerate) (PHB-HV);
(d) poly(caprolactone) (PCL);
(e) poly(L-lactide-co-glycolide) (PLGA);
(f) poly(D,L-lactide-co-glycolide);
(g) and AB and ABA block-copolymers of PEG with poly (butylene terephthalate) (PBT), e.g., poly(ethylene-glycol)-block-poly(butyleneterephthalate) (PEG-PBT), poly(ethylene-glycol)-block-poly (butylene terephthalate)-block-poly (ethylene-glycol) (PEG-PBT-PEG), or poly(butyleneterephthalate)-block-poly(ethylene-glycol)-block poly(butyleneterephthalate) (PBT-PEG-PBT); and (h) AB and ABA block-copolymers of PEG with PCL, e.g., poly(ethylene-glycol)-block-poly(caprolactone) (PEG-PCL), poly(ethylene-glycol)-block-poly(caprolactone)-block-poly(ethylene-glycol) (PEG-PCL-PEG), or poly(caprolactone)-block-poly(ethylene-glycol)-block-poly(caprolactone) (PCL-PEG-PCL).

Any mixture of compounds of groups (a)-(h) described above can be also used. PEG-PBT and PEG-PBT-PEG block copolymers are known under a trade name POLYACTIVE and are available from IsoTis Corp. of Holland. These polymers can be obtained, for example, by trans-esterification of dibutyleneterephthalate with PEG. In POLYACTIVE, the ratio between the units derived from ethylene glycol and the units derived from butylene terephthalate can be between about 0.67:1 and about 9:1. The molecular weight of the units derived from ethylene glycol can be between about 300 and about 4,000 Daltons, and the molecular weight of the units derived from butylene terephthalate can be between about 50,000 and about 250,000, for example, about 100,000 Daltons.

DLPLA-PEG-DLPLA, PEG-DLPLA-PEG, PEG-PBT, PEG-PBT-PEG, PBT-PEG-PBT, PEG-PCL, PEG-PCL-PEG, and PCL-PEG-PCL block copolymers all contain fragments with ester bonds. Ester bonds are known to be water-labile bonds. When in contact with slightly alkaline blood, ester bonds are subject to catalyzed hydrolysis, thus ensuring biological degradability of the block-copolymer. One product of degradation of every block polymer, belonging to the group DLPLA-PEG-DLPLA, PEG-DLPLA-PEG, PEG-PBT, PEG-PBT-PEG, PBT-PEG-PBT, PEG-PCL, PEG-PCL-PEG, and PCL-PEG-PCL is expected to be PEG, which is highly biologically compatible.

Any layer of the stent coating can contain any amount of the bioabsorbable polymer(s) described above, or a blend of more than one of such polymers. If less than 100% of the layer is made of the bioabsorbable polymer(s) described above, other, alternative, polymers can comprise the balance. Examples of the alternative polymers that can be used include polyacrylates, such as poly(butyl methacrylate), poly(ethyl methacrylate), poly(ethyl methacrylate-co-butyl methacrylate), poly(acrylonitrile), poly(ethylene-co-methyl methacrylate), poly(acrylonitrile-co-styrene), and poly(cyanoacrylates); fluorinated polymers and/or copolymers, such as poly(vinylidene fluoride) and poly(vinylidene fluoride-co-hexafluoropropylene); poly(N-vinyl pyrrolidone); polydioxanone; polyorthoester; polyanhydride; poly(glycolic acid); poly(glycolic acid-co-trimethylene carbonate); polyphosphoester; polyphosphoester urethane; poly(amino acids); poly(trimethylene carbonate); poly(iminocarbonate); co-poly(ether-esters); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; vinyl halide polymers and copolymers, such as polyvinyl chloride; polyvinyl ethers, such as polyvinyl methyl ether; polyvinylidene chloride; polyvinyl ketones; polyvinyl aromatics such as polystyrene; polyvinyl esters such as polyvinyl acetate; copolymers of vinyl monomers with each other and olefins, e.g., poly(ethylene-co-vinyl alcohol) (EVAL); ABS resins; and poly(ethylene-co-vinyl acetate); polyamides such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Representative examples of some solvents suitable for making the stent coatings include N,N-dimethylacetamide (DMAC), N,N-dimethylformamide (DMF), tethrahydrofuran (THF), cyclohexanone, xylene, toluene, acetone, i-propanol, ethanol, methyl ethyl ketone, propylene glycol monomethyl ether, methyl butyl ketone, ethyl acetate, n-butyl acetate, and dioxane. Some solvent mixtures can be used as well. Representative examples of the mixtures include:

(1) DMAC and methanol (e.g., a 50:50 by mass mixture);

(2) water, i-propanol, and DMAC (e.g., a 10:3:87 by mass mixture);

(3) i-propanol, and DMAC (e.g., 80:20, 50:50, or 20:80 by mass mixtures);

(4) acetone and cyclohexanone (e.g., 80:20, 50:50, or 20:80 by mass mixtures);

(5) acetone and xylene (e.g. a 50:50 by mass mixture);

(6) acetone, FLUX REMOVER AMS, and xylene (e.g., a 10:50:40 by mass mixture); and (7) 1,1,2-trichloroethane and chloroform (e.g., an 80:20 by mass mixture).

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer being dissolved.

The therapeutic substance which can be used in the reservoir layer can include any substance capable of exerting a therapeutic or prophylactic effect for a patient. The therapeutic substance may include small molecule substances, peptides, proteins, oligonucleotides, and the like. The therapeutic substance could be designed, for example, to inhibit the activity of vascular smooth muscle cells. It can be directed at inhibiting abnormal or inappropriate migration and/or proliferation of smooth muscle cells to inhibit restenosis.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, myolimus, novolimus, biolimus, deforolimus, temsirolimus, ABT-578 and 40-O-tetrazole-rapamycin.

The coatings and methods of the present invention have been described with reference to a stent, such as a balloon expandable or self-expandable stent. The use of the coating is not limited to stents, however, and the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), L-605, stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. In some embodiments, the device itself can be made from the above described polymers.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

3. Examples

The following examples are provided to further illustrate embodiments of the present invention.

Example 1

A first composition can be prepared by mixing the following components:
(a) between about 1.0 mass % and about 15 mass %, for example, about 2.0 mass % poly(D,L-lactic acid) (DLPLA) having inherent viscosity of about 0.67 dl/cm³ at room temperature, and (b) the balance, a solvent blend comprising 1,1,2-trichloroethane (TCE) and chloroform having a mass ratio between TCE and chloroform of about 4:1.

The first composition can be applied onto the surface of a bare 12 mm VISION stent (available from Guidant Corporation) by spraying and dried to form a primer layer. A spray coater can be used having a 0.014 fan nozzle maintained at about 60° C. with a feed pressure of about 0.2 atm (about 3 psi) and an atomization pressure of about 1.3 atm (about 20 psi). The primer can be baked at about 120° C. for about 30 minutes, yielding a dry primer layer. The primer layer can contain about 100 μg DLPLA.

A second composition can be prepared by mixing the following components:
(a) between about 0.05 mass % and about 3.0 mass %, for example, about 2.0 mass % EVEROLIMUS; and
(c) the balance, a solvent blend comprising acetone and xylene having a mass ratio between acetone and xylene of about 2:3.

The second composition can be applied onto the dried primer layer to form the reservoir layer, using the same spraying technique and equipment used for applying the primer layer, followed by drying, e.g., by baking at about 50° C. for about 1 hour, yielding a dry reservoir layer. The dry reservoir layer can contain about 120 μg EVEROLIMUS.

A third composition can be prepared by mixing the following components:
(a) between about 1.0 mass % and about 15 mass %, for example, about 2.0 mass % DLPLA having inherent viscosity of about 0.67 dl/cm³ at room temperature, and
(b) the balance, a solvent blend comprising TCE and chloroform having a mass ratio between TCE and chloroform of about 4:1.

The third composition can be applied onto the dried reservoir layer to form a topcoat layer, using the same spraying technique and equipment used for applying the primer layer and the reservoir layer followed by drying, e.g., by baking at about 50° C. for about 1 hour, yielding a dry topcoat layer. The dry topcoat layer can contain about 300 μg DLPLA.

Example 2

A 12 mm VISION stent can be coated as described in Example 1. A composition can be prepared by mixing the following components:
(a) between about 1.0 mass % and about 15 mass %, for example, about 2.0 mass % PEG-PBT having about 45 molar % PBT units and about 55 molar % PEG units. The molecular weight of the PEG units can be about 300 Daltons, and the molecular weight of the PBT blocks can be about 100,000 Daltons; and
(b) the balance, the blend of TCE and chloroform described above.

The composition can be applied onto the dried stent coating with which the stent had been coated to form the finishing coat layer, using the same spraying technique and equipment used for applying the primer layer, followed by drying, e.g., by baking at about 50° C. for about 1 hour, yielding a dry finishing coat layer. The dry finishing coat layer can contain about 150 μg PEG-PBT.

Example 3

The stent can be coated with a primer layer as described in Example 1. A first composition can be prepared by mixing the following components:

(a) between about 0.05 mass % and about 3.0 mass %, for example, about 0.7 mass % EVEROLIMUS;

(b) between about 1.0 mass % and about 15 mass %, for example, about 2.1 mass % DLPLA having inherent viscosity of about 0.67 dl/cm³ at room temperature, and (c) the balance, the blend of TCE and chloroform described above.

The mass ratio between EVEROLIMUS and DLPLA can be about 1:3. The first composition can be applied onto the dried primer layer to form the reservoir layer, using the same spraying technique and equipment used for applying the primer layer, followed by drying, e.g., by baking at about 50° C. for about 1 hour, yielding a dry reservoir layer. The dry reservoir layer can contain about 75 μg EVEROLIMUS and about 225 μg DLPLA.

A second composition can be prepared by mixing the following components:

(a) between about 1.0 mass % and about 15 mass %, for example, about 2.0 mass % DLPLA having inherent viscosity of about 0.67 dl/cm³ at room temperature, and (b) the balance, the blend of TCE and chloroform described above.

The second composition can be applied onto the dried reservoir layer to form a topcoat layer, using the same spraying technique and equipment used for applying the primer layer and the reservoir layer followed by drying, e.g., by baking at about 50° C. for about 1 hour, yielding a dry topcoat layer. The dry topcoat layer can contain about 100 μg DLPLA.

Example 4

The stent can be coated following the same procedures as described in Example 3, except in the reservoir layer DLPLA can be replaced with the carboxylated DLPLA (DLPLA-COOH) which can be obtained from Birmingham Polymers, Inc. The dry reservoir layer can contain about 75 μg EVEROLIMUS and about 225 μg DLPLA-COOH.

Example 5

Synthesis of DLPLA-PEG-DLPLA Block-Copolymer

About 33 mmol of PEG diol having molecular weight of about 3,400 Daltons and about 33 mol of D,L-lactide re-crystallized from acetone were placed in a flask and dissolved in anhydrous toluene. An azeotropic distillation was performed twice under vacuum to remove residual water. The blend of PEG-diol and D,L-lactide was heated to about 140° C. under vacuum for about 10 minutes. The vacuum was under about 7 Torr. While the temperature was maintained at about 140° C., argon was introduced into the flask and a catalytic amount of stannous octoate (2 drops, gauge 21 needle) was added to the blend of PEG-diol and D,L-lactide as the argon atmosphere in the flask was maintained. The reaction was then carried out for about 10 hours at the temperature of about 160° C. The resulting polymer was dissolved in acetone, precipitated in methanol, and vacuum-dried at about 60° C. for about 72 hours.

Example 6

The stent can be coated with a primer layer as described in Example 1. A first composition can be prepared by mixing the following components:

(a) between about 0.05 mass % and about 3.0 mass %, for example, about 0.7 mass % EVEROLIMUS;

(b) between about 1.0 mass % and about 15 mass %, for example, about 2.1 mass % poly(lactic acid)-block-poly(ethylene glycol)-block-poly(lactic acid) (DLPLA-PEG-DLPLA) described in Example 5; and (c) the balance, the blend of TCE and chloroform described above.

The mass ratio between EVEROLIMUS and DLPLA-PEG-DLPLA can be about 1:3. The first composition can be applied onto the dried primer layer to form the reservoir layer, using the same spraying technique and equipment used for applying the primer layer, followed by drying, e.g., by baking at about 50° C. for about 1 hour, yielding a dry reservoir layer. The dry reservoir layer can contain about 75 μg EVEROLIMUS and about 225 μg DLPLA-PEG-DLPLA.

A second composition can be prepared by mixing the following components:

(a) between about 1.0 mass % and about 15 mass %, for example, about 2.0 mass % PEG-PBT block-copolymer described in Example 2; and (b) the balance, the blend of TCE and chloroform described above.

The second composition can be applied onto the dried reservoir to form the topcoat layer, using the same spraying technique and equipment used for applying the primer layer and reservoir, followed by drying, e.g., by baking at about 50° C. for about 1 hour, yielding a dry topcoat layer. The dry topcoat layer can contain about 150 μg PEG-PBT.

Example 7

The stent can be coated with a primer layer as described in Example 1. A first composition can be prepared by mixing the following components:

(a) between about 0.05 mass % and about 3.0 mass %, for example, about 0.7 mass % EVEROLIMUS;

(b) between about 1.0 mass % and about 15 mass %, for example, about 2.1 mass % DLPLA;

(c) between about 0.05 mass % and about 3.0 mass %, for example, about 0.7 mass % PEG terminated on both ends with an amino group (PEG-diamine); and (d) the balance, the blend of TCE and chloroform described above.

PEG-diamine adduct can be obtained from Huntsman Chemical Co. of Houston, Tex. under the trade name JEFFAMINE. The mass ratio between EVEROLIMUS, DLPLA, and PEG-diamine can be about 1:3:1. The first composition can be applied onto the dried primer layer to form the reservoir layer, using the same spraying technique and equipment used for applying the primer layer, followed by drying, e.g., by baking at about 50° C. for about 1 hour, yielding a dry reservoir layer. The dry reservoir layer can, contain about 60 μg EVEROLIMUS, about 60 μg PEG-diamine and about 180 μg DLPLA. A topcoat layer can then be formed over the dried reservoir as described in Example 6.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

Embodiments of the present invention include the following:

1. a medical article comprising an implantable substrate having a coating, the coating including a polymer comprising a derivative of poly(lactic acid), or a block-copolymer having at least one moiety derived from poly(lactic acid).

2. The medical article of embodiment 1, wherein the medical article is a stent.

3. The medical article of embodiment 1, wherein poly(lactic acid) includes poly(D-lactic acid), poly(L-lactic acid), or poly(D,L-lactic acid).

4. The medical article of embodiment 1, wherein the derivative of poly(lactic acid) is hydrolyzed poly(lactic acid), or carboxylated poly(lactic acid).

5. The medical article of embodiment 1, wherein the block-copolymer includes a diblock-copolymer, a triblock-copolymer, or mixtures thereof 6. The medical article of embodiment 5, wherein the diblock-copolymer and triblock-copolymer include at least one biocompatible moiety.

7. The medical article of embodiment 6, wherein the biocompatible moiety is poly(ethylene glycol).

8. The medical article of embodiment 6, wherein the biocompatible moiety is selected from a group consisting of poly(ethylene oxide), polypropylene glycol), poly(tetramethylene glycol), polyethylene oxide-co-propylene oxide), ε-caprolactone, β-butyrolactone, δ-valerolactone, glycolide, poly(N-vinyl pyrrolidone), poly(acrylamide methyl propane sulfonic acid) and salts thereof, poly(styrene sulfonate), sulfonated dextran, polyphosphazenes, poly(orthoesters), poly(tyrosine carbonate), hyaluronic acid or derivatives thereof, copolymers of poly(ethylene glycol) with hyaluronic acid or derivatives thereof, heparin, copolymers of polyethylene glycol with heparin, a graft copolymer of poly(L-lysine) and poly(ethylene glycol).

9. The medical article of embodiment 5, wherein the diblock-copolymer is a copolymer having a formula

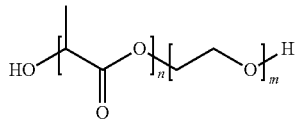

wherein each of "n" and "m" is an integer.

10. The medical article of embodiment 9, wherein "n" has a value between about 21 and about 278, and "m" has a value between about 11 and about 682.

11. The medical article of embodiment 5, wherein the triblock-copolymer is a copolymer having a formula

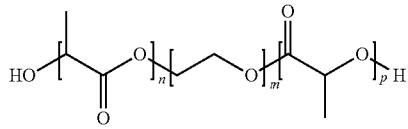

wherein each of "n," "m," and "p" is an integer.

12. The medical article of embodiment 11, wherein "n" has a value between about 21 and about 278, and "m" has a value between about 11 and about 682, and "p" has a value between about 21 and about 278.

13. The medical article of embodiment 5, wherein the triblock-copolymer is a copolymer having a formula

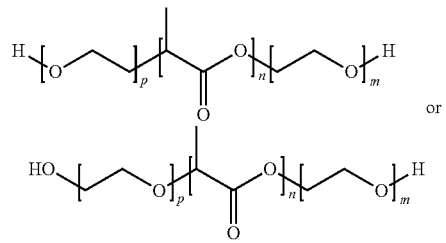

wherein each of "n," "m," and "p" is an integer.

14. The medical article of embodiment 13, wherein "n" has a value between about 21 and about 278, "m" has a value between about 11 and about 682, and "p" has a value between about 11 and about 682.

15. The medical article of embodiment 5, wherein the diblock-copolymers and triblock-copolymers are hydrolyzed block-copolymers of poly(lactic acid) and poly(ethylene glycol).

16. The medical article of embodiment 1, wherein the coating further includes a biologically absorbable polymer.

17. The medical article of embodiment 16, wherein the biologically absorbable polymer is selected from a group consisting of poly(hydroxybutyrate), poly(hydroxyvalerate), poly(hydroxybutyrate-co-valerate), poly(caprolactone), poly(lactide-co-glycolide), poly(ethylene-glycol)-block-poly(butyleneterephthalate), poly(ethylene-glycol)-block-poly(butylene terephthalate)-block-polyethylene-glycol), poly(butyleneterephthalate)-block-poly(ethylene-glycol)-block poly(butyleneterephthalate), poly(ethylene-glycol)-block-poly(caprolactone), poly(ethylene-glycol)-block-poly(caprolactone)-block-poly(ethylene-glycol), poly(caprolactone)-block-poly(ethylene-glycol)-block-poly(caprolactone), and blends thereof 18. The medical article of embodiment 1, additionally comprising a biologically active agent incorporated into the coating.

19. A method for fabricating a medical article, the method including depositing a coating on at least a portion of an implantable substrate, the coating including a polymer comprising a derivative of poly(lactic acid), or a block-copolymer having at least one moiety derived from poly(lactic acid).

20. The method of embodiment 19, wherein the medical article is a stent.

21. The method of embodiment 19, wherein poly(lactic acid) includes poly(D-lactic acid), poly(L-lactic acid), or poly(D,L-lactic acid).

22. The method of embodiment 19, further including hydrolyzing or carboxylating poly(lactic acid) to obtain the derivative of poly(lactic acid).

23. The method of embodiment 19, wherein the block-copolymer includes a diblock-copolymer, a triblock-copolymer, or mixtures thereof.

24. The method of embodiment 23, wherein the diblock-copolymer and triblock-copolymer include at least one biocompatible moiety.

25. The method of embodiment 24, wherein the biocompatible moiety is poly(ethylene glycol).

26. The method of embodiment 24, wherein the biocompatible moiety is selected from a group consisting of poly(ethylene oxide), polypropylene glycol), poly(tetramethylene glycol), poly(ethylene oxide-co-propylene oxide), ε-caprolactone, β-butyrolactone, δ-valerolactone, glycolide, poly(N-vinyl pyrrolidone), poly(acrylamide methyl propane sulfonic acid) and salts thereof, poly(styrene sulfonate), sulfonated dextran, polyphosphazenes, poly(orthoesters), poly(tyrosine carbonate), hyaluronic acid or derivatives thereof, copolymers of poly(ethylene glycol) with hyaluronic acid or derivatives thereof, heparin, copolymers of polyethylene glycol with heparin, a graft copolymer of poly(L-lysine) and poly(ethylene glycol).

27. The method of embodiment 23, wherein the diblock-copolymer is a copolymer having a formula

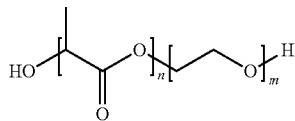

wherein each of "n" and "m" is an integer.

28. The method of embodiment 27, wherein "n" has a value between about 21 and about 278, and "m" has a value between about 11 and about 682.

29. The method of embodiment 23, wherein the triblock-copolymer is a copolymer having a formula

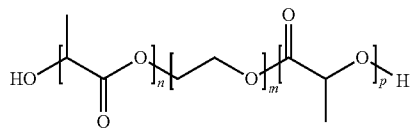

wherein each of "n," "m," and "p" is an integer.

30. The method of embodiment 29, wherein "n" has a value between about 21 and about 278, and "m" has a value between about 11 and about 682, and "p" has a value between about 21 and about 278.

31. The method of embodiment 23, wherein the triblock-copolymer is a copolymer having a formula

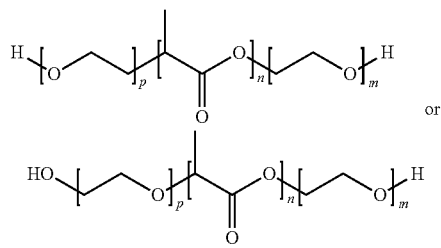

wherein each of "n," "m," and "p" is an integer.

32. The method of embodiment 31, wherein "n" has a value between about 21 and about 278, "m" has a value between about 11 and about 682, and "p" has a value between about 11 and about 682.

33. The method of embodiment 23, further including hydrolyzing the diblock-copolymers and triblock-copolymers to obtain hydrolyzed block-copolymers of poly(lactic acid) and poly(ethylene glycol), and incorporating the hydrolyzed block-copolymers of poly(lactic acid) and poly(ethylene glycol) into the coating.

34. The method of embodiment 19, further including incorporating a biologically absorbable polymer.

35. The method of embodiment 34, wherein the biologically absorbable polymer is selected from a group consisting of poly(hydroxybutyrate), poly(hydroxyvalerate), poly(hydroxybutyrate-co-valerate), poly(caprolactone), poly(lactide-co-glycolide), poly (ethylene-glycol)-block-poly(butyleneterephthalate), poly(ethylene-glycol)-block-poly(butylene terephthalate)-block-poly(ethylene-glycol), poly(butyleneterephthalate)-block-poly(ethylene-glycol)-block poly(butyleneterephthalate), polyethylene-glycol)-block-poly(caprolactone), polyethylene-glycol)-block-poly(caprolactone)-block-poly(ethylene glycol), poly(caprolactone)-block-poly(ethylene-glycol)-block-poly(caprolactone), and blends thereof 36. The method of embodiment 19, additionally comprising incorporating a biologically active agent into the coating.

What is claimed is:

1. A medical article comprising an implantable substrate having a coating, the coating including a polymer comprising a carboxylated poly(lactic acid), or a block-copolymer having at least one moiety comprising a carboxylated poly(lactic acid), wherein the carboxylated poly(lactic acid) is of formula (D):

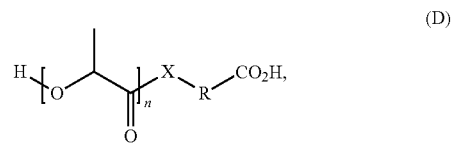

wherein

X is selected from the group consisting of O, NH, and S;

R is phenyl; and n is an integer;

wherein the molecular weight of the carboxylated poly(lactic acid) is about 1,000 to about 20,000 Daltons;

wherein the block-copolymer is a diblock-copolymer or a triblock-copolymer comprising at least one biocompatible moiety, wherein the biocompatible moiety is selected from a group consisting of poly(tetramethylene glycol), β-butyrolactone, δ-valerolactone, poly(N-vinyl pyrrolidone), poly(acrylamide methyl propane sulfonic acid) and salts thereof, poly(styrene sulfonate), sulfonated dextran, poly(tyrosine carbonate), hyaluronic acid, copolymers of poly(ethylene glycol) with hyaluronic acid, heparin, copolymers of polyethylene glycol with heparin, a graft copolymer of poly(L-lysine) and poly(ethylene glycol).

2. The medical article of claim 1, wherein the medical article is a stent.

3. The medical article of claim 1, wherein polylactic acid) includes poly(D-lactic acid), poly(L-lactic acid), or poly(D, L-lactic acid).

4. The medical article of claim 1, wherein the carboxylated poly(lactic acid) is of formula (C):

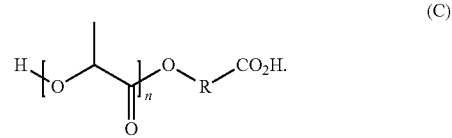

5. The medical article of claim 1, wherein the carboxylated poly(lactic acid) is of formula (E):

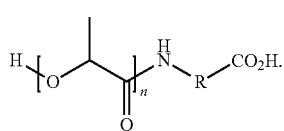
(E)

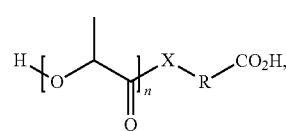
(D)

6. The medical article of claim 1, wherein the carboxylated poly(lactic acid) is of formula (F):

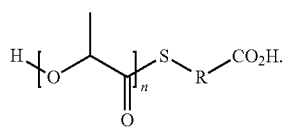
(F)

7. The medical article of claim 1, wherein the biocompatible moiety is selected from a group consisting of poly(N-vinyl pyrrolidone), poly(acrylamide methyl propane sulfonic acid) and salts thereof, poly(styrene sulfonate), sulfonated dextran, and poly(tyrosine carbonate).

8. The medical article of claim 1, wherein the biocompatible moiety is poly(tetramethylene glycol), hyaluronic acid, copolymers of poly(ethylene glycol) with hyaluronic acid, heparin, copolymers of polyethylene glycol with heparin, and a graft copolymer of poly(L-lysine) and poly(ethylene glycol).

9. The medical article of claim 1, wherein the coating further includes a biologically absorbable polymer.

10. The medical article of claim 9, wherein the biologically absorbable polymer is selected from a group consisting of poly(hydroxybutyrate), poly(hydroxyvalerate), poly(hydroxybutyrate-co-valerate), poly(caprolactone), poly(lactide-co-glycolide), poly(ethylene-glycol)-block-poly(butyleneterephthalate), poly(ethylene-glycol)-block-poly(butylene terephthalate)-block-poly(ethylene-glycol), poly(butyleneterephthalate)-block-poly(ethylene-glycol)-block poly(butyleneterephthalate), poly(ethylene-glycol)-block-poly(caprolactone), poly(ethylene-glycol)-block-poly(caprolactone)-block-poly(ethylene-glycol), poly(caprolactone)-block-poly(ethylene-glycol)-block-poly (caprolactone), and blends thereof.

11. The medical article of claim 1, additionally comprising a biologically active agent incorporated into the coating.

12. A method for fabricating a medical article, the method including depositing a coating on at least a portion of an implantable substrate, the coating including a polymer comprising a carboxylated poly(lactic acid), or a block-copolymer having at least one moiety comprising a carboxylated poly(lactic acid)),wherein the carboxylated poly(lactic acid) is of formula D:

wherein
X is selected from the group consisting of O, NH, and S;
R is phenyl; and
n is an integer;
wherein the molecular weight of the carboxylated poly(lactic acid) is between about 1,000 and about 20,000 Daltons;
wherein the block-copolymer is a diblock-copolymer or a triblock-copolymer including at least one biocompatible moiety,
wherein the biocompatible moiety is selected from a group consisting of poly(tetramethylene glycol), β-butyrolactone, δ-valerolactone, poly(N-vinyl pyrrolidone), poly(acrylamide methyl propane sulfonic acid) and salts thereof, poly(styrene sulfonate), sulfonated dextran, poly(tyrosine carbonate), hyaluronic acid, copolymers of poly(ethylene glycol) with hyaluronic acid, heparin, copolymers of polyethylene glycol with heparin, a graft copolymer of poly(L-lysine) and poly(ethylene glycol).

13. The method of claim 12, wherein the medical article is a stent.

14. The method of claim 12, wherein polylactic acid) includes poly(D-lactic acid), poly(L-lactic acid), or poly(D, L-lactic acid).

15. The method of claim 12, wherein the biocompatible moiety is selected from a group consisting of poly(N-vinyl pyrrolidone), poly(acrylamide methyl propane sulfonic acid) and salts thereof, poly(styrene sulfonate), sulfonated dextran, and poly(tyrosine carbonate).

16. The method of claim 12, further including incorporating a biologically absorbable polymer.

17. The method of claim 16, wherein the biologically absorbable polymer is selected from a group consisting of poly(hydroxybutyrate), poly(hydroxyvalerate), poly(hydroxybutyrate-co-valerate), poly(caprolactone), poly(lactide-co-glycolide), poly (ethylene-glycol)-block-poly(butyleneterephthalate), poly(ethylene-glycol)-block-poly (butylene terephthalate)-block-poly(ethylene-glycol), poly(butyleneterephthalate)-block-poly(ethylene-glycol)-block poly(butyleneterephthalate), poly(ethylene-glycol)-block-poly(caprolactone), polyethylene-glycol)-block-poly(caprolactone)-block-poly(ethylene glycol), poly(caprolactone)-block-poly(ethylene-glycol)-block-poly(caprolactone), and blends thereof.

18. The method of claim 12, additionally comprising incorporating a biologically active agent into the coating.

* * * * *